(12) United States Patent
Lee et al.

(10) Patent No.: US 6,572,608 B1
(45) Date of Patent: *Jun. 3, 2003

(54) DIRECTIONAL LASER PROBE

(76) Inventors: Eric T. Lee, 6400 Christie Ave., Apt. 2105, Emeryville, CA (US) 94608; Patrick S. Jensen, 3 Wellhaven Cir. #1228, Owings Mills, MD (US) 21117; Anthony D. Cornetto, III, 406 Crane's Roost Ct., Annapolis, MD (US) 21401; Terry H. Shelley, 4291 Northwoods Trail, Hampstead, MD (US) 21074; Carl C. Awh, 441 Belle Pointe Dr., Nashville, TN (US) 37221; Eugene de Juan, Jr., 13721 Poplar Hill Rd., Phoenix, MD (US) 21131; Michael D. Auld, 16201 Pepper View Ct., Chesterfield, MO (US) 63005; Gregg D. Scheller, 17820 Suzanne Ridge Dr., Wildwood, MO (US) 63038

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/545,143

(22) Filed: Apr. 7, 2000

Related U.S. Application Data

(60) Provisional application No. 60/128,265, filed on Apr. 8, 1999.

(51) Int. Cl.[7] .............................................. A61B 18/18
(52) U.S. Cl. ................................ 606/15; 606/4; 606/13; 606/78

(58) Field of Search ........................... 606/4–6, 13–16, 606/166, 78; 607/88, 89; 128/898

(56) References Cited

U.S. PATENT DOCUMENTS

| | | | | |
|---|---|---|---|---|
| 4,347,837 A | * | 9/1982 | Hosono | 128/6 |
| 4,674,497 A | * | 6/1987 | Ogasawara | 128/303.1 |
| 4,744,360 A | * | 5/1988 | Bath | 128/303.1 |
| 5,172,685 A | * | 12/1992 | Nudelman | 128/6 |
| 5,469,524 A | * | 11/1995 | Esch et al. | 385/118 |
| 5,520,222 A | * | 5/1996 | Chikama | 138/118 |
| 5,603,710 A | * | 2/1997 | Easley et al. | 606/15 |
| 5,656,011 A | * | 8/1997 | Uihlein et al. | 600/146 |
| 5,688,264 A | * | 11/1997 | Ren et al. | 606/15 |
| 5,855,577 A | * | 1/1999 | Marphy-Chutorian et al. | 606/7 |
| 5,865,831 A | * | 2/1999 | Cozean et al. | 606/6 |
| 5,957,916 A | * | 9/1999 | Jeevanandam et al. | 606/15 |
| 5,993,072 A | * | 11/1999 | De Juan, Jr. et al. | 385/78 |
| 6,053,911 A | * | 4/2000 | Ryan et al. | 606/33 |
| 6,142,990 A | * | 11/2000 | Burk | 606/6 |

FOREIGN PATENT DOCUMENTS

DE  198 24 786 A1  * 1/1999  ............ A61C/1/08

* cited by examiner

Primary Examiner—Linda C. M. Dvorak
Assistant Examiner—A. Farah
(74) Attorney, Agent, or Firm—Thompson Coburn LLP

(57) ABSTRACT

A microsurgical laser probe is provided with a distal end portion of an optic fiber that projects from a tubular sleeve of the probe and can be caused to bend relative to the probe sleeve by manual manipulation of a mechanism on a handle of the probe.

20 Claims, 2 Drawing Sheets

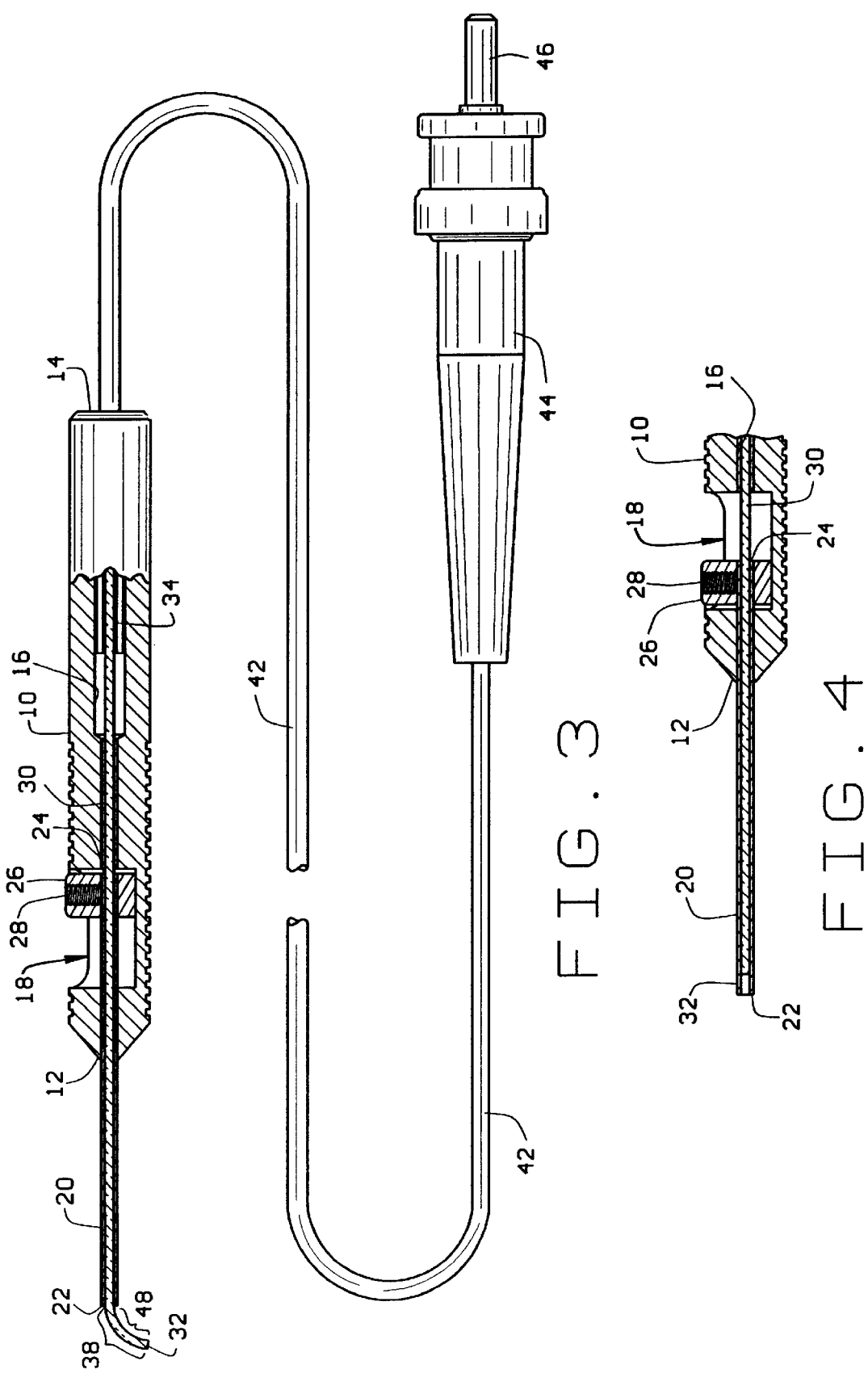

DIRECTIONAL LASER PROBE

This application claims the benefit of Provisional Application No. 60/128,265, filed Apr. 8, 1999.

BACKGROUND OF THE INVENTION (1) Field of the Invention

The present invention pertains to a microsurgical laser probe used primarily in ophthalmic surgery. The probe has a handle and a tubular sleeve and a distal end portion of an optic fiber projecting from the sleeve can be caused to bend relative to the sleeve by manual manipulation of a mechanism on the probe handle.

(2) Description of the Prior Art

In ophthalmic surgery, various different types of instruments are available for use by the surgeon to transmit laser energy to a surgical site in the interior of the eye. The typical microsurgical laser probe comprises a handle with a small cylindrical metal sleeve projecting from a distal end of the handle. An optic fiber, having a proximal end with a connector for coupling to a source of laser light, passes through the center of the handle and the sleeve of the probe. The distal end of the optic fiber is positioned adjacent the distal end of the sleeve. In instruments of this type, the sleeve can project straight from the handle of the instrument or can have a slight bend or curve as it projects from the instrument handle.

Efficient delivery of laser light in the eye interior toward the anterior or front portion of the retina is often awkward to the surgeon using a straight laser probe. This is due to the positioning of the incision or instrument entry site in the eye relative to the target area or surgical site of the laser light being transmitted. This is illustrated in FIG. 1 where an area A of the eye interior is inaccessible to the straight tip of the laser probe shown. The use of curved laser probes such as that shown in FIG. 2 allows for a greater range of coverage inside the eye, thereby minimizing the risk of hitting the lens of the eye with the laser light and overcoming the disadvantages of the straight sleeve laser probe discussed above. However, curved laser probes cannot be inserted through straight cannulas and therefore must be directed through the eye incision site itself.

The optimal deliver of laser light to a surgical site in the eye requires that the laser be directed perpendicular to the target area of the surgical site. Directing a straight laser probe at anterior or forward portions of the retina causes the approach angle, or angle of incidence of the laser light, to be large. In this situation the optimal delivery of laser light to the surgical site cannot be achieved. Additionally, torquing or manipulating the tubular sleeve of the straight probe in the entry incision to reduce the angle of approach of the laser light to the surgical site in these awkward areas often produces excessive, and sometimes harmful stresses around the incision of the eye. Often the only way for the surgeon to overcome this situation is to create a second incision site for insertion of the laser probe. These problems can be overcome by using a curved laser probe that can effectively eliminate the use of a secondary incision site since an increased area in the eye interior is accessible from the single entry site as illustrated in FIG. 2. Currently available curved laser probes are able to access more anterior or forward areas of the eye interior than can be achieved with straight laser probes. However, because their curvatures are fixed, curved laser probes are not efficient at directing laser energy to areas even more anterior or more forward in the eye that would require a tighter bend or curvature of the probe sleeve, or areas at the far end or posterior of the retina which would require a straight sleeve laser probe due to the approach angle.

To overcome these disadvantages of prior art straight and curved laser probes, what is needed is an adjustable directional laser probe that is capable of reducing the approach angle or angle of incidence of light toward the surgical site, thereby providing ease of access and reduced instrument manipulation at the target site, reduced tissue stress at the point of entry, and improved laser focusing by directing the laser energy more perpendicular to the target surgical site.

SUMMARY OF THE INVENTION

The directional laser probe of the present invention may be constructed having either a disposable hand piece or a reusable hand piece and, although described as transmitting laser light, it may also be employed in transmitting light for illumination. The directional laser probe makes use of a shape memory metal alloy, nitinol, to steer and direct a flexible optic fiber to a surgical target site. Alternative shape memory materials such as spring steel or plastics may also be used. Whether the target site lies in the posterior or anterior portions of the eye interior, the directional laser probe can easily deflect to any angle between 0° (or a straight configuration) and 90° or more. The flexible nature of the nitinol alloy allows variable adjustment of the bend angle of the probe to deliver laser energy to the target site. Additionally, cannulas may be used in the incision site of the eye because the laser probe, when in its straight configuration, can be inserted through the cannula to position the tip of the probe in the interior of the eye, and then a bend can be created at the tip of the probe in the eye interior. The directional laser probe is especially useful when accessing anterior portions of the retina, or areas that are difficult or awkward to access using traditional straight probes.

The directional laser probe of the invention is basically comprised of a handle having an interior bore passing through its center and having a recess formed in a side of the handle communicating with the interior bore. A tubular sleeve projects from a distal end of the handle and is received in the bore for axial sliding movement relative to the handle. A finger pad positioned in the recess is connected to the sleeve and manipulating the finger pad axially through the recess causes the sleeve to be moved between a pushed forward position where it projects its greatest distance from the distal end of the handle, and a pulled back position where the sleeve projects its shortest distance from the distal end of the handle. A tubular nitinol tip passes through the sleeve and is secured stationary relative to the handle. A length of optic fiber enters the handle bore at the handle proximal end and a distal end portion of the optic fiber passes through the bore and the nitinol tip. The proximal end of the fiber is connected to a standard light source connector, for example a SMA type connector.

The nitinol tip that passes through the sleeve is annealed in a pre-bent 90° bend in its preferred embodiment. When the finger pad of the instrument is pushed forward, it extends the sleeve to its pushed forward position in which the nitinol tip and the distal end portion of the optic fiber are completely contained inside the tubular sleeve. When the finger pad is moved to its pulled back position, the sleeve is also moved back to its pulled back position causing the bent portion of the nitinol tip and the distal end portion of the optic fiber to be gradually exposed at the distal end of the sleeve. As the nitinol tip and the optic fiber contained therein are exposed at the end of the sleeve, they gradually bend from the initial straight configuration of the sleeve toward the 90° pre-bent configuration of the nitinol tip. In this manner, the optic fiber contained in the nitinol tip can be adjustably positioned through any angle between 0° when the nitinol tip and optic fiber are entirely contained in the tubular sleeve at its pushed forward position, to a 90° bend when the nitinol tip and optic fiber project from the sleeve distal end with the sleeve moved to its pulled back position.

In use of the directional laser probe, the optic fiber connector is first attached to a laser power source. With the finger pad in its pushed forward position, the optic fiber is contained in the sleeve which projects in a straight line from the distal end of the handle. The sleeve is then inserted through a cannula positioned in an incision in the eye or inserted directly through the incision, positioning the sleeve in the eye interior. The finger pad is then slowly moved toward the rear of the handle causing the sleeve to slowly move toward its pulled back position relative to the handle. This, in turn, causes the distal end portion of the optic fiber contained in the pre-bent portion of the tubular nitinol tip to gradually bend from its straight configuration toward its 90° configuration. The bending of the fiber allows optimal positioning of the fiber tip to areas where a straight fiber may not reach. Rotation of the entire instrument about its center axis may be necessary to further direct the optic fiber tip. Once the proper location of the fiber tip is achieved, laser energy can then be delivered to the site of interest. Retraction of the fiber tip into the sleeve is performed by first pushing the finger pad forward, causing the sleeve to move toward its pushed forward position and causing straightening of the bent portion of the optic fiber projecting from the sleeve. With the optic fiber contained in the sleeve, the sleeve is then pulled back through the surgical entry site.

DESCRIPTION OF THE DRAWINGS

Further objects and features of the present invention will be revealed in the following detailed description of the preferred embodiment of the invention and in the drawing figures, wherein:

FIG. 3 is a partially sectioned view of the directional laser probe of the invention with the curved optic fiber projecting from the probe sleeve;

FIG. 4 is a partial sectioned view of the instrument sleeve with the optic fiber in its straight configuration;

DETAILED DESCRIPTION OF THE PREFERRED EMBODIMENT

Figure 1:
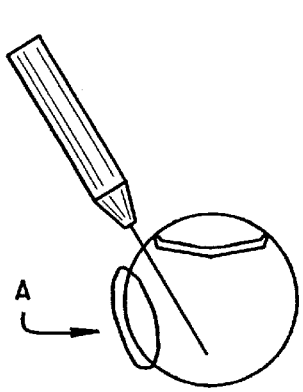
FIG. 1 is an illustration of a conventional straight laser probe employed in ophthalmic surgery.
Figure 2:
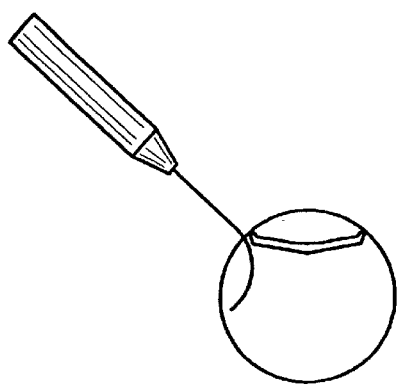
FIG. 2 is a view similar to FIG. 1 but showing a conventional curved laser probe.

The directional laser probe of the invention is described herein as transmitting laser light for use in laser surgery of the eye. However, the probe is equally well suited for use in transmitting light for illumination. In addition, the probe can be designed as a disposable instrument or as a reusable instrument.

The directional laser probe is provided with an elongated narrow handle or hand piece 10 having opposite distal 12 and proximal 14 ends. The handle 10 is dimensioned to a size similar to that of a pencil to fit comfortably in the surgeon's hand. The handle is preferably manufactured of a disposable medical grade plastic. A hollow bore 16 extends through the center of the handle from its distal end 12 to its proximal end 14. The bore 16 enlarges slightly adjacent the proximal end 14 of the handle. A recess 18 is formed into a side of the handle and intersects the center bore 16. The recess 18 extends axially along a short length of the handle forming an axial slot.

A cylindrical narrow tube or sleeve 20 of stainless steel is received in the bore 16 at the distal end 12 of the handle for sliding movement of the sleeve 20 through the bore. The sleeve 20 projects from the handle distal end 12 to a distal end 22 of the sleeve. The opposite proximal end 24 of the sleeve is positioned in the recess or slot 18 of the handle.

A finger pad 26 is positioned in the slot 18 for axial sliding movement of the finger pad through the slot between a pushed forward position of the finger pad 26 shown in FIG. 4 and a pulled back position of the finger pad shown in FIG. 3. The finger pad 26 is preferably constructed of disposable medical grade plastic. The finger pad has a hole into which the sleeve proximal end 24 is inserted. A set screw 28 secures the finger pad 26 to the proximal end 24 of the sleeve. Thus, moving the finger pad 26 to its pushed forward position shown in FIG. 4 will also move the sleeve 20 through the handle bore 16 to its forward most position or pushed forward position relative to the handle 10 where it projects its greatest distance from the handle distal end 12. Moving the finger pad 26 to its pulled back position shown in FIG. 3 will also move the sleeve 20 to its pulled back position relative to the handle 10 where the sleeve distal end 22 projects its shortest distance from the handle distal end 12. In the preferred embodiment of the invention, the travel distance of the finger pad 26 in the slot 18 and of the sleeve distal end 22 is 25 mm.

Figure 5:
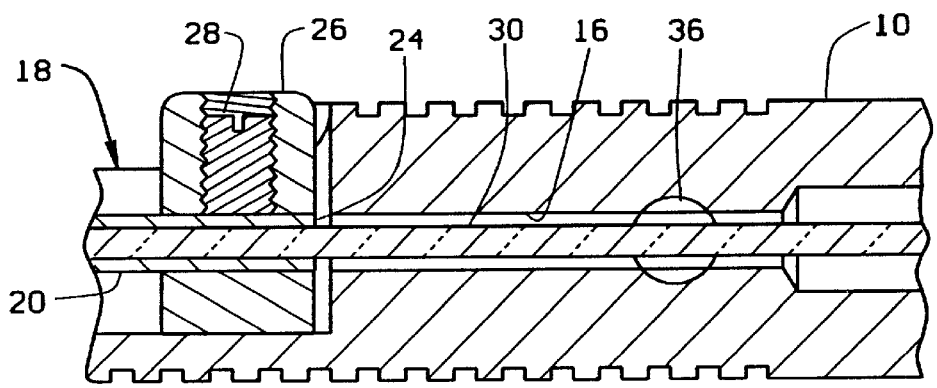
FIG. 5 is a partial sectioned view showing the connections of the sleeve and optic fiber in the instrument handle.
Figure 6:
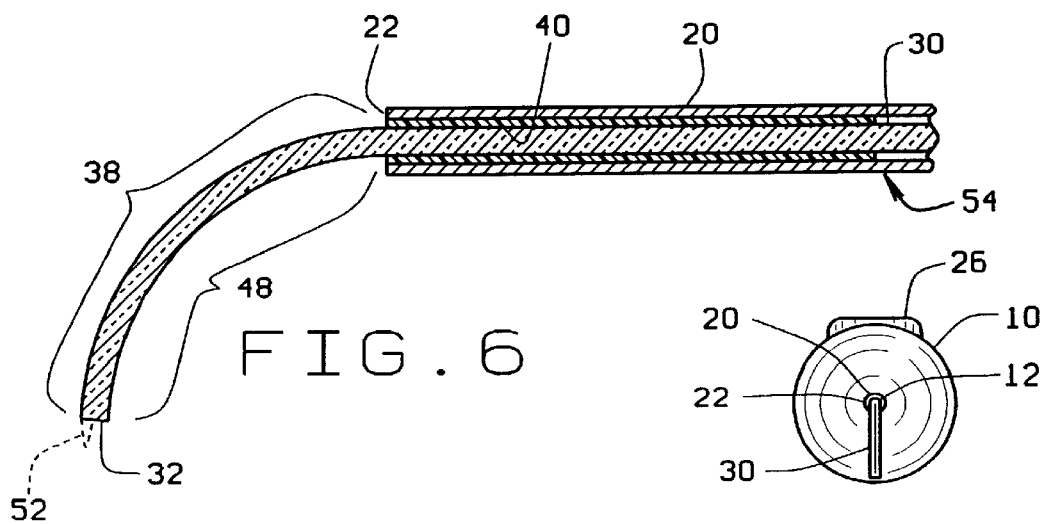
FIG. 6 is a partial sectioned view showing the detail of the optic fiber in its curved configuration.
Figure 7:
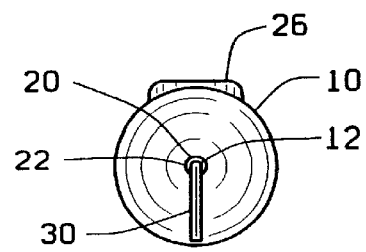
FIG. 7 is an end view of the instrument handle showing the optic fiber in its curved configuration.

A narrow tubular tip 30 constructed of the shape memory metal alloy nitinol extends through the center of the sleeve 20 and a portion of the handle bore 16. Alternatively, the tubular tip 30 could be constructed of other shape memory materials such as spring steel or plastics. The overall length of the tip 30 is slightly larger than the length of the sleeve 20. The tip 30 is positioned in the sleeve 20 and the handle center bore 16 so that a distal end 32 of the tip is positioned just inside the sleeve distal end 22 when the sleeve is moved to its forward most position shown in FIG. 4. The nitinol tip 30 passes through the slot 18 in the side of the handle and extends for a short distance through the center bore 16 behind the slot. As shown in FIG. 5, the tip proximal end 34 is secured stationary relative to the handle 10 by a set screw 36 that passes through the side of the handle and engages against the exterior of the tip 30. With the tip distal end 32 being positioned just inside the distal end 22 of the sleeve when the sleeve is moved to its pushed forward position, a distal end portion of the tip 30 projects from the sleeve distal end 22 when the finger pad 26 and the sleeve 20 are moved to their pulled back positions shown in FIG. 3. The distal end portion 38 of the nitinol tip 30 that projects from the sleeve distal end 22 is shown in FIG. 6. This distal end portion 38 of the tip is pre-bent as shown in FIG. 6 so that it will curve through an angle of 90° relative to the straight sleeve 20 when the sleeve is moved completely to its pulled back position as shown in FIG. 6. Other pre-bent angles of the tip greater than 90° or less than 90° may also be used. To obtain the 90° bend, the distal end portion 38 of the nitinol tip is bent in the configuration shown in FIG. 6 and is then heated to its annealing temperature (roughly 550° Celsius). Thus, when the finger pad 26 and the sleeve 20 are moved to their pulled back positions shown in FIGS. 3 and 6, the distal end portion 38 of the tip that projects from the distal end 22 of the sleeve gradually bends through 90° to its position shown in FIG. 6. By pushing the finger pad 26 and the sleeve 20 to their pushed forward position shown in FIG. 4, the distal end portion 38 of the tip is moved back into the interior of the sleeve 20 and the sleeve straightens out the bend in the tip distal end portion as it is moved to its position relative to the sleeve shown in FIG. 4.

To assist the sliding of the sleeve 20 over the distal end portion 38 of the tip, the interior of the sleeve is coated with a layer 40 of a sliding material such as Teflon®. The sliding material layer 40 extends only a short distance in the sleeve interior adjacent the sleeve distal end 22. The remainder of the sleeve interior is dimensioned slightly larger than the exterior diameter of the tubular nitinol tip 30 providing an air gap between the tip exterior and the sleeve interior. The layer of sliding material and the air gap both reduce actuation drag and enhance the ease of sliding the sleeve 20 over the exterior of the tip 30.

A length of optic fiber 42 extends between the handle 10 and a connector 44. The length of optic fiber 42 between the handle 10 and the connector 44 is protected by a layer of cladding as is conventional. The proximal end 46 of the optic fiber enters the connector 44 and its cladding is removed. The exposed portion of optic fiber extends entirely through the connector 44 and its proximal end is positioned adjacent the end of the ferrule 46 projecting from the connector 44 as is conventional in optic fiber microsurgical instruments. The distal end of the optic fiber 42 enters the center bore 16 of the handle at the handle proximal end 14. Inside the handle center bore 16 the protective cladding of the optic fiber is removed and the optic fiber enters the proximal end 34 of the tubular nitinol tip 3. The exposed optic fiber extends entirely through the nitinol tip 30 to the distal end of the tip 32. In the preferred embodiment the tip of the optic fiber extends past the tubular nitinol tip distal end 32 by 0.25 mm. With the optic fiber passing entirely through the nitinol tip 30, a distal end portion 48 of the optic fiber inside the tip distal end portion 38 is also bent through the 90° angle of the tip as the tip is bent through the 90° angle. Thus, when the finger pad 26 of the instrument is pushed forward, it extends the sleeve 20 to its pushed forward position in which the nitinol tip 30 and the distal end portion 48 of the optic fiber are completely contained inside the sleeve and are held in the straight configuration of the sleeve. When the finger pad 26 is moved to its pulled back position, the sleeve 20 is also moved back to its pulled back position causing the bent portion of the nitinol tip 30 and the distal end portion 48 of the optic fiber contained therein to be gradually exposed at the distal end of the sleeve. As the nitinol tip and the optic fiber are exposed at the end of the sleeve, they gradually bend from the initial straight configuration of the sleeve toward the 90° pre-bent configuration of the nitinol tip. In this manner, the optic fiber contained in the nitinol tip can be adjustably positioned through any angle between 0° when the nitinol tip and the optic fiber are entirely contained in the tubular sleeve at its pushed forward position, to a 90° bend when the nitinol tip and the optic fiber project from the sleeve distal end with the sleeve moved to its pulled back position.

In use of the directional laser probe, the optic fiber connector 44 is first attached to a laser power source. With the finger pad 26 in its pushed forward position, the optic fiber is contained in the sleeve 20 which projects in a straight line from the distal end of the handle. The sleeve 20 is then inserted through a cannula positioned in an incision in the eye or inserted directly through the incision positioning the sleeve in the eye interior. The finger pad 26 is then slowly moved toward the rear of the handle causing the sleeve 20 to slowly move toward its pulled back position relative to the handle. This, in turn, causes the distal end portion 48 of the optic fiber contained in the pre-bent portion 38 of the nitinol tip to gradually bend from its straight configuration toward its 90° configuration. The bending of the fiber allows optimal positioning of the fiber tip to areas where a straight fiber may not reach. Rotation of the entire instrument about its center axis may be necessary to further direct the optic fiber tip. Once the proper location of the fiber tip is achieved, laser energy can then be delivered to the site of interest. Retraction of the tip is performed by first pushing the finger pad 26 forward causing the sleeve 20 to move toward its pushed forward position and causing straightening of the bent portion 48 of the optic fiber projecting from the sleeve. With the optic fiber contained in the sleeve, the sleeve is then pulled back through the surgical entry site.

In alternate embodiments of the invention the distal end 32 of the nitinol tip could be provided with a tool such as an extension pick 52 represented by dashed lines in FIG. 6. In addition, as set forth earlier, other shape memory materials could be used to construct the tip and the tip can be pre-bent to different angles. The sleeve 20 could also be mounted stationary relative to the handle 10 and the pre-bent tip 30 containing the optic fiber could be made moveable relative to the sleeve and handle to adjust the bend in the tip. Also, the sleeve 20 could be provided with a hole 54 for injection or suction of fluids through the hole 54 and the air gap created between the nitinol tip exterior surface and the sleeve interior surface behind the Teflon® layer 40. Furthermore, the actuation mechanism provided by the finger pad 26 can be replaced with other types of mechanisms that would produce the same axial movement of the sleeve 20, for example by a trigger mechanism manipulated by the surgeon's finger or by a squeeze mechanism that is squeezed by the surgeon's hand. In addition, a fiducial mark could be provided on the sleeve adjacent its distal end 22 to indicate to the surgeon which direction the distal end portion 38 of the tip will bend as it is extended out of the distal end 22 of the sleeve. This would be useful to the surgeon in accurately positioning the sleeve in the interior of the eye before the bending movement of the nitinol tip is commenced.

The above-described directional laser probe is intended for use as a disposable instrument. If the laser probe is to be reusable, the only difference in the construction is in the dimension of the optic fiber that passes through the instrument. The instrument can also be used as a steerable light source or as a directional laser probe depending upon the particular optic fiber inserted into the handle prior to use. To accommodate various light fiber sizes, the tubular nitinol tip 30 and the sleeve 20 could be increased to a larger diameter. An illumination optic fiber or a laser fiber would then be fed into the proximal end 14 of the handle and positioned in the tubular nitinol tip 30. A plug would be provided at the distal end 32 of the nitinol tip to securely fix the distal end of the optic fiber in the tip.

While the present invention has been described by reference to a specific embodiment, it should be understood that modifications and variations of the invention may e constructed without departing from the scope of the invention defined in the following claims.

What is claimed:

1. A surgical instrument comprising:

an instrument handle;

a tubular sleeve projecting from the instrument handle;

an optic fiber extending through the handle and the sleeve to a distal end portion that projects from the sleeve, the distal end portion of the optic fiber having an adjustable bend therein;

the handle has a mechanism that is connected to the sleeve and selectively moves the sleeve between pushed forward and pulled back positions of the sleeve relative to the handle; and, the sleeve is a rigid tube that projects from the handle and the distal end portion of the optic fiber has a preformed bend that is straightened when the sleeve is moved to the pushed forward position causing the distal end portion to be retracted into the tube of the sleeve and the preformed bend bends when the sleeve is moved to the pulled back position causing the distal end portion to be extended from the tube of the sleeve.

2. The instrument of claim 1, wherein:

the optic fiber is held stationary relative to the handle and in the pushed forward position of the sleeve the distal end portion of the optic fiber is entirely contained in the sleeve and in the pulled back position of the sleeve the distal end portion of the optic fiber projects from the sleeve.

3. The instrument of claim 1, wherein:

the distal end of the optic fiber is contained in a tubular tip, the tubular tip has a pre-bent portion and is constructed of a shape memory material.

4. The instrument of claim 3 wherein:

the tip is constructed of nitinol and extends through the sleeve and is secured stationary to the handle.

5. The instrument of claim 1, wherein:

the optic fiber is the only optic fiber that passes through the handle and the sleeve.

6. The instrument of claim 1, wherein:

the instrument is an illuminating probe.

7. The instrument of claim 1, wherein:

the instrument is a laser probe.

8. The instrument of claims 1, wherein:

the tubular sleeve has an interior surface and there is an air gap between the sleeve interior surface and the optic fiber in the sleeve.

9. The instrument of claim 1, wherein:

the tubular sleeve has an interior surface and a layer of sliding material between the sleeve interior surface and the optic fiber in the sleeve.

10. The instrument of claim 9, wherein:

the layer of sliding material is located in only a portion of the sleeve creating an air gap between the sleeve interior surface and the optic fiber where the layer of sliding materiel is not located.

11. A surgical instrument comprising:

an instrument handle;

a tubular sleeve projecting from the handle;

an optic fiber extending through the handle and the sleeve to a distal end portion of the fiber;

a mechanism on the handle and connected to the sleeve to selectively move the sleeve between a pushed forward position of the sleeve where the sleeve projects a first distance from the handle and the optic fiber distal end portion is retracted into the sleeve and a pulled back position of the sleeve where the sleeve projects a second distance from the handle that is less than the first distance and the optic fiber distal end portion is extended from the sleeve; and the sleeve is a rigid tube that projects from the handle and the distal end portion of the optic fiber has a preformed bend that is straightened when the distal end portion is retracted into the tube of the sleeve and bends when the distal end portion is extended from the tube of the sleeve.

12. The instrument of claim 11, wherein:

the optic fiber is secured stationary to the handle and the distal end portion of the optic fiber projects from the sleeve when the sleeve is moved to the pulled back position and the distal end portion of the optic fiber is entirely contained in the sleeve when the sleeve is moved to the pushed forward position.

13. The instrument of claim 11, wherein:

the distal end portion of the fiber is contained in a tubular tip that has the bend formed therein and is constructed of a shape memory material.

14. The instrument of claim 13, wherein:

the tip is constructed of nitinol and is secured stationary to the handle.

15. The instrument of claim 11, wherein:

the sleeve projects straight from the handle and the distal end portion of the optic fiber bends relative to the sleeve as it projects from the sleeve.

16. The instrument of claim 11, wherein:

the optic fiber is the only optic fiber that passes through the handle and the sleeve.

17. The instrument of claim 11, wherein:

the instrument is a laser probe.

18. The instrument of claim 11, wherein:

the tubular sleeve has an interior surface and there is an air gap between the sleeve interior surface and the optic fiber in the sleeve.

19. The instrument of claim 11, wherein:

the tubular sleeve has an interior surface and a layer of sliding material between the sleeve interior surface and the optic fiber in the sleeve.

20. The instrument of claim 19, wherein:

the layer of sliding material is located in only a portion of the sleeve creating an air gap between the sleeve interior surface and the optic fiber where the layer of sliding materiel is not located.

* * * * *

UNITED STATES PATENT AND TRADEMARK OFFICE
CERTIFICATE OF CORRECTION

PATENT NO. : 6,572,608 B1
DATED : June 3, 2003
INVENTOR(S) : Lee et al.

It is certified that error appears in the above-identified patent and that said Letters Patent is hereby corrected as shown below:

Signed and Sealed this

Twenty-first Day of June, 2005

JON W. DUDAS
*Director of the United States Patent and Trademark Office*

UNITED STATES PATENT AND TRADEMARK OFFICE
CERTIFICATE OF CORRECTION

PATENT NO.    : 6,572,608 B1
DATED         : June 3, 2003
INVENTOR(S)   : Lee et al.

Page 1 of 1

It is certified that error appears in the above-identified patent and that said Letters Patent is hereby corrected as shown below:

Column 7,
Line 21, Claim 3 should read:
The instrument of Claim 1, wherein:
    the sleeve projects straight from the handle and the distal end portion of the optic fiber bends relative to the sleeve as it projects from the sleeve.

Signed and Sealed this

Second Day of August, 2005

JON W. DUDAS
*Director of the United States Patent and Trademark Office*